United States Patent
White et al.

(10) Patent No.: US 6,169,289 B1
(45) Date of Patent: Jan. 2, 2001

(54) SIGNAL ENHANCEMENT FOR FLUORESCENCE MICROSCOPY

(75) Inventors: John G. White; David L. Wokosin, both of Madison, WI (US)

(73) Assignee: Wisconsin Alumni Research Foundation, Madison, WI (US)

(*) Notice: Under 35 U.S.C. 154(b), the term of this patent shall be extended for 0 days.

(21) Appl. No.: 09/236,885

(22) Filed: Jan. 25, 1999

Related U.S. Application Data

(60) Provisional application No. 60/072,771, filed on Jan. 27, 1998.

(51) Int. Cl.[7] .................................................. G01N 21/64
(52) U.S. Cl. .................................... 250/458.1; 250/459.1; 250/461.1
(58) Field of Search .............................. 250/458.1, 459.1, 250/461.1

(56) References Cited

U.S. PATENT DOCUMENTS

| | | |
|---|---|---|
| 3,541,542 | 11/1970 | Duguay et al. . |
| 4,349,907 | 9/1982 | Campillo et al. . |
| 5,032,720 | 7/1991 | White . |
| 5,034,613 | 7/1991 | Denk et al. . |
| 5,035,476 | 7/1991 | Ellis et al. . |
| 5,260,578 | 11/1993 | Bliton et al. . |
| 5,289,407 | 2/1994 | Strickler et al. . |
| 5,296,700 | 3/1994 | Kumagai . |
| 5,296,703 | 3/1994 | Tsien . |
| 5,377,003 | 12/1994 | Lewis et al. . |
| 5,386,112 | 1/1995 | Dixon . |
| 5,523,573 | 6/1996 | Hänninen et al. . |
| 5,583,342 | 12/1996 | Ichie . |
| 5,777,732 | 7/1998 | Hanninen et al. . |
| 5,796,112 | 8/1998 | Ichie . |

FOREIGN PATENT DOCUMENTS

| | | |
|---|---|---|
| 2532756 | 3/1984 | (FR) . |
| 61-138146 | 6/1984 | (JP) . |
| WO 97/11355 | 3/1997 | (WO) . |

OTHER PUBLICATIONS

Winfried Denk, et al., "Two–Photon Laser Scanning Fluorescence Microscopy," Science, vol. 248, Apr. 6, 1990, pp. 73–76.

Winfried Denk, et al., "Two–Photon Molecular Excitation in Laser Scanning Microscopy," Handbook of Biological Confocal Microscopy, Plenum Press, New York, 1995, Chapter 28, pp. 445–458.

*Primary Examiner*—Constantine Hannaher
*Assistant Examiner*—Andrew Israel
(74) *Attorney, Agent, or Firm*—Foley & Lardner

(57) ABSTRACT

Multi-photon excitation fluorescence microscopy is carried out by focusing an excitation beam by an objective lens onto a specimen and collecting the multi-photon fluorescence light emitted from the specimen to the objective lens and directing the fluorescent light on an optical path to a detector. Fluorescent light emissions from the specimen collected by a condenser lens on the opposite side of the specimen from the objective lens are directed to a dichoic mirror, which reflects the light photons back into the condenser lens and thence into and through the objective lens where they are directed on an optical path to the detector. Significantly increased fluorescent photon collection efficiency is obtained as well as improved image intensity of the detected fluorescent light.

19 Claims, 4 Drawing Sheets

SIGNAL ENHANCEMENT FOR FLUORESCENCE MICROSCOPY

This application claims the benefit of provisional patent application Ser. No. 60/072,771, filed Jan. 27, 1998, which is incorporated herein by reference.

This invention was made with United States government support awarded by the following agency: NIH Grant No. RR00570-26S1. The United States government has certain rights in this invention.

FIELD OF THE INVENTION

This invention pertains generally to the field of microscopy and particularly to laser scanning fluorescence microscopy.

BACKGROUND OF THE INVENTION

Scanning optical microscopes, such as laser scanning confocal microscopes, are of increasing importance in microscopy, particularly for imaging of dynamic biological structures such as living cells. In a scanning microscope, the light beam from the source, usually a laser, is focussed to a point within the specimen by the microscope objective and the specimen and beam are moved relative to one another in a raster fashion, either by moving the stage on which the specimen is mounted or, more commonly, by deflecting the light beam so that it scans across a stationary specimen. The light from the specimen is collected by the objective and passed back through the microscope to a detector, such as a photomultiplier tube. In addition to detection of light reflected from a specimen (or transmitted through the specimen), scanning microscopes can also be constructed to detect fluorescence induced by the illuminating light beam. Typically, the fluorophores in the specimen absorb the illumination light, which is at a chosen wavelength (usually shorter wavelength visible light), and fluorescently emit photons at a longer wavelength which are received by the objective of the microscope and passed back through the scanning optics to a dichroic mirror which separates the fluorescent light from the reflected light and directs the fluorescent light to a separate photodetector. In this manner, particular structures within the specimen, such as parts of cells, can be labeled with fluorescent markers and distinctively imaged by the scanning microscope.

Where the scanning fluorescence microscope operates by using moving mirrors or other deflectors to deflect the light beam to scan across the specimen, the light emitted from the specimen is typically passed back through the scanning system (descanned) before being separated from the source light beam by a dichroic mirror and directed to the detector. In a confocal scanning fluorescence microscope, the incoming beam is typically passed through an aperture before entering the scanning system, and the emitted light beam, after being descanned, is focussed through a confocal pinhole aperture before being incident upon the detector. The confocal aperture blocks light from portions of the specimen outside of the focal plane so that substantially only light from the focal plane is incident on the detector, thereby greatly improving the depth resolution. Thus, the image data received from the photodetector for storage and/or display comprises image information from substantially only the focal plane. By focussing the incident light on a specimen at different focal planes, a three-dimensional image of a semi-transparent specimen, such as a living cell, can be built up.

Most fluorophores can also absorb two (or more) photons of longer wavelengths simultaneously when sufficiently intense illumination light is applied thereto and will emit a fluorescent photon at a shorter wavelength than the incident light. This phenomenon is exploited in multi-photon laser scanning microscopes in which an incident beam of relatively long wavelength light in short pulses from a laser source is narrowly focussed onto a specimen so that the light reaches an intensity at the focal point sufficient to excite detectable two (or more) photon fluorescence. The emitted fluorescent photons collected by the objective lens of the microscope are passed back through the optical system, either through the scanning optics to a dichroic mirror which reflects light at longer wavelengths while passing the shorter wavelength fluorescent light to a separate detector, or by bypassing the scanning system and directing the light from the microscope objective lens to a dichroic mirror which passes the shorter wavelength fluorescent light directly to a detector while reflecting the longer wavelength excitation light. See, Winfried Denk, et al., "Two Photon Laser Scanning Fluorescence Microscopy," Science, Vol. 248, 6 April 1990, pp. 73–76; Winfried Denk, et al., "Two-Photon Molecular Excitation in Laser-Scanning Microscopy," Chapter 28, Handbook of Biological Confocal Microscopy, Plenum Press, New York, 1995, pp. 445–458; and U.S. Pat. No. 5,034,613 entitled Two-Photon Laser Microscopy.

By focussing the incident light from the objective lens to a relatively narrow spot or waist such that the intensity of the incident light is sufficient to excite multi-photon excitation only at the waist within the specimen, multi-photon fluorescence excitation will occur generally only in the focal plane. The shorter wavelength fluorescent light emitted by the specimen can then be passed back, either through the scanning system to descan the light or directly, without descanning, to a fluorescent light detector to obtain an image corresponding to the focal plane. Therefore, the excitation light alone produces the desired depth resolution (i.e., an optically sectioned fluorescence image), so that there is no need for the use of a confocal aperture. The fluorophore excitation is typically restricted to the minimum required to form an optical section fluorescence image thereby minimizing photobleaching and phototoxicity in thick tissues due to fluorophore excitation. The quality of the images obtained in such fluorescence microscope, particularly for live cell imaging, is dependent on the collection of as much of the fluorescence signal as possible. A limitation of scanning fluorescence microscopes generally, including those using two photon fluorescence excitation, is that the amount of fluorescent light collected from the specimen by the microscope objective may be relatively low.

SUMMARY OF THE INVENTION

In accordance with the invention, multi-photon excitation fluorescence microscopy is carried out with significantly increased fluorescent photon collection efficiency and improved image intensity of the available fluorescent signal. Such increased collection efficiency is obtained without requiring an increase in the intensity of the incident excitation light beam. Optionally, the intensity of the incident excitation beam can be reduced while still obtaining comparable image information to thereby reduce photolysis and photobleaching caused by the incident light beam on specimens such as living cells. Such increased fluorescent signal collection efficiency is obtained without requiring the use of an additional photodetector or a major modification of existing laser scanning fluorescent microscope designs, and without inhibiting or affecting the functionality of such microscopes in their epi-illumination transmitted light imaging modes.

A scanning multi-photon fluorescent microscope in accordance with the invention receives light from a laser source that includes a chosen long wavelength, typically a pulsed laser providing short pulses of light in red or near infrared wavelengths, and directs the beam of excitation light from the source on an optical path to the back aperture of an objective lens of a microscope, which focusses the incident beam to a narrow point or waist inside a specimen to be examined. Fluorophores in the specimen absorb two (or more) photons at the wavelength of the incident light and emit—in a random direction—a fluorescent photon at a lower wavelength (higher energy) than the incident light. The fluorescent photons that are emitted from the specimen toward the objective lens are collected by the objective lens and directed back in a beam to a first dichroic mirror which is formed to pass (or, alternatively, reflect) the shorter wavelength fluorescent light to direct such light to a detector such as a photomultiplier tube. The dichroic mirror is further formed to substantially reflect (or, alternatively, pass) wavelengths of light above a selected wavelength including light at the incident beam wavelength. The detector is positioned with respect to the dichroic mirror so that the detector only receives the fluorescent light emanated from the spot on the specimen being scanned at which the incoming beam is focussed and does not detect the reflected light or the incoming beam.

Typical biological samples being examined in the microscope, such as cells or cell components, are semi-transparent. Thus, fluorescent light photons will be emitted from the specimen at the point of focus of the incident beam randomly in all directions, and a portion of these photons will be emitted in a direction in which they can be collected by a condenser lens of the microscope that is mounted on the opposite side of the specimen from the objective lens. Typically, the specimen may be mounted upon a stage or support that is transparent to the fluorescent light photons, such as a glass slide. The fluorescent light photons entering the condenser lens are collected and directed in a beam to a second dichroic mirror, which is formed to reflect wavelengths shorter than a selected wavelength (or range of wavelengths), the reflected wavelengths including the fluorescent light wavelength, and to pass light at wavelengths longer than the selected wavelength or range, the passed wavelengths including the wavelength of the incident excitation beam. The second dichroic mirror is preferably mounted at the position of the condenser and field iris of the microscope so as to reflect the maximum light back to the condenser lens and, if desired, the light at the incident beam wavelength that is passed through the second dichroic mirror may be directed to a detector, allowing transmitted light image data to be collected from the beam that is scanned over the specimen.

The fluorescent light photons reflected from the second dichroic mirror are collected by the condenser and are passed back through the specimen (and the slide on which it is mounted) and then through the objective lens, which directs these reflected fluorescent photons along the main optical axis of the microscope back to the first dichroic mirror, through which such photons pass so as to be incident upon the fluorescent light detector. The fluorescent photons that are reflected from the second dichroic mirror and pass back through the condenser lens, the specimen, and the objective lens add to the photons that are directly emitted from the specimen to the objective lens, providing an enhanced intensity signal from the fluorescent light photodetector. Significantly, it is found in accordance with the present invention that a relatively large percentage of the photons emitted from the specimen toward the condenser are passed back through the lenses of the microscope and the specimen without excessive absorption, thereby significantly increasing the intensity of the signal from the fluorescent light photodetector, with intensity improvements in the 45 to 70 percent range being typical.

The present invention may be incorporated in a microscope which achieves scanning of the specimen by x-y mechanical displacement of the specimen stage and the specimen relative to a fixed beam. The invention may also be incorporated in typical laser scanning microscopes in which the incident beam is scanned in an x-y raster fashion over a stationary specimen. In such scanned beam microscopes, the first dichroic mirror is preferably mounted in a position to deflect the beam from the scanning optics within the microscope and to direct the moving beam to the back aperture of the objective lens of the microscope. The fluorescent light passed back from the objective lens then passes through the first dichroic mirror and is focussed to reimage the back aperture of the objective lens onto a fluorescent light photodetector. In such an epi-fluorescence arrangement, a confocal aperture for the fluorescent beam passed through the first dichroic mirror is not required. The invention may also be incorporated in a microscope in which the first dichroic mirror is mounted at a position to receive the beam from the source and to reflect that beam into the scanning optics, which then directs the x-y rastered beam to the objective lens of the microscope. In such an epi-fluorescent arrangement, the fluorescent light is passed back through the optical system of the microscope and is fully descanned before reaching the first dichroic mirror, through which it passes to be incident upon the fluorescent light photodetector. While a confocal aperture may be utilized in such systems, in the present invention it is neither necessary nor preferred since such an aperture would reduce the total flux of fluorescent light photons that are incident upon the photodetector. While not needed, the confocal aperture can be used to increase depth resolution of sectioning, if desired.

Further objects, features and advantages of the invention will be apparent from the following detailed description when taken in conjunction with the accompanying drawings.

DETAILED DESCRIPTION OF THE INVENTION

Figure 1:
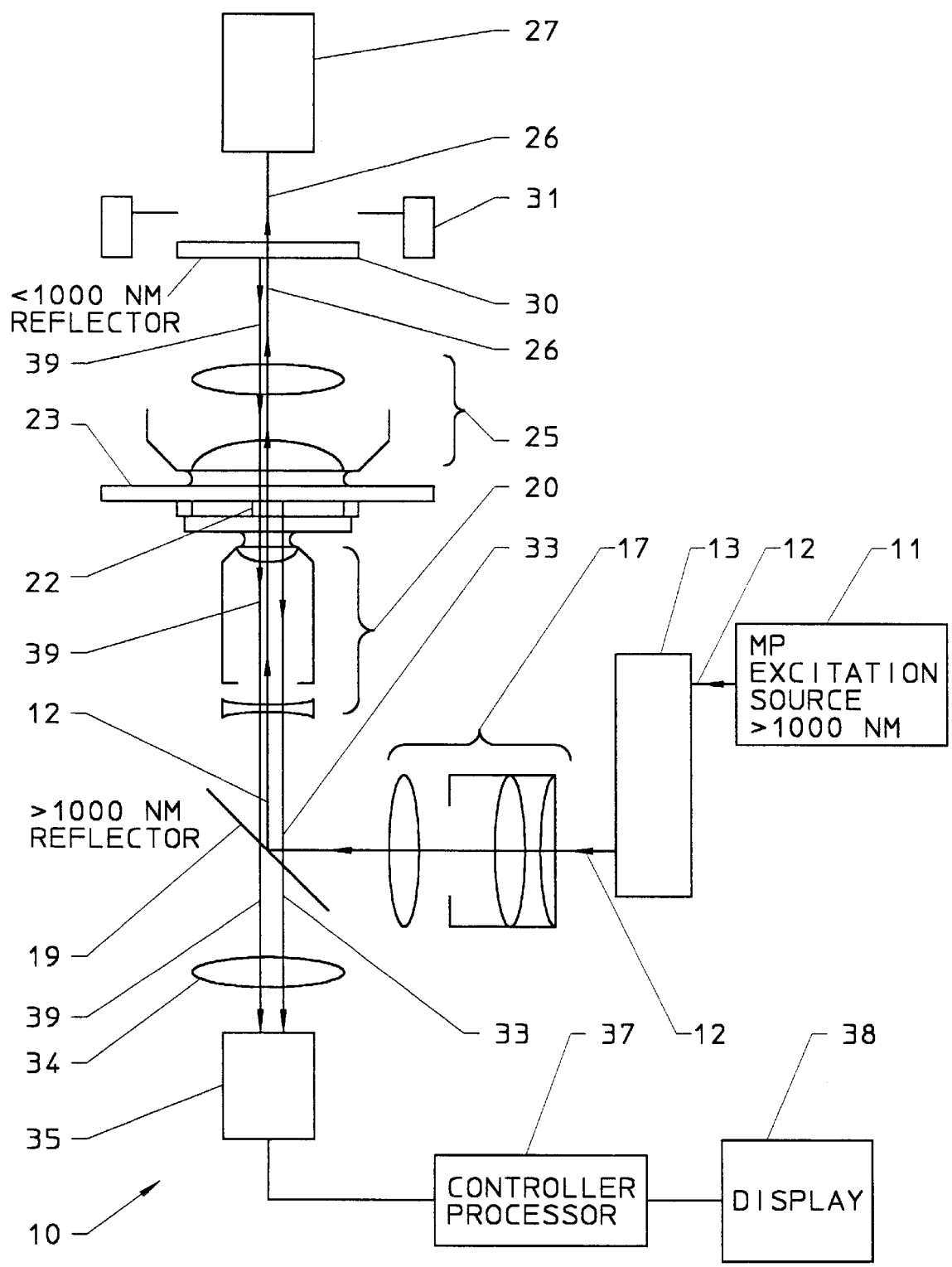
FIG. 1 is a schematic diagram of a multi-photon scanning fluorescence microscope in accordance with the invention.

With reference to the drawings, a multi-photon excitation fluorescence microscope incorporating the present invention is shown generally at 10 in FIG. 1. The microscope system 10 receives excitation light from a source 11, typically a pulsed laser providing light in the red or near infrared range, and directs the laser output beam 12 to a scanning system 13 which may include, for example, orthogonally rotatable mirrors and which deflect the beam 12 in a raster fashion. An exemplary scanning system is described in U.S. Pat. No. 5,032,720 to John G. White entitled Confocal Imaging System, incorporated herein by reference, but any suitable scanning system may be utilized. An example is a BioRad MRC-600 confocal scanning system coupled to a Nikon Diaphot 200 Quantum microscope (an inverted microscope with a bottom access port "Keller hole") via a broadband antireflective-coated achromatic lens with a 150 mm focal length. Alternatively, the beam may be fixed and the stage holding the specimen may be moved. The beam then passes on an optical path through conventional telescope optics 17 to a first dichroic mirror 19 which directs the beam 12 into the objective lens 20 of the microscope. The objective lens 20 focusses the incident beam 12 onto a focal spot or waist within a specimen 22 held on a substrate 23 (such as a transparent microscope slide). The incident light that passes through the specimen 22 and the substrate 23 is received by a microscope condenser lens 25 which passes a light beam 26 that is the portion of the incident beam 12 that has passed through both the specimen and the slide, toward, for example, a transmitted light detector 27 (e.g., a photodiode). In accordance with the present invention, a second dichroic mirror 30 is mounted to receive the light passed through the condenser lens 25 and is constructed so that light above a selected wavelength, including the wavelengths of the excitation light in the beam 12 provided by the source 11, passes therethrough so that the beam 26 is substantially transmitted and can be received by the detector 27. The dichroic mirror 30 is a planar mirror as shown in FIG. 1 and preferably mounted at the field iris 31 of the microscope. It is highly preferred that the second dichroic mirror 30 be mounted at the field iris because the iris is at a conjugate of the focal plane in the specimen and all signals from a spot on the image are focussed at this plane, and thus the incident light will be reflected (but inverted) back by the mirror 30 and will be captured by the condenser lens. As discussed further below, the mirror 30 is constructed so as to substantially reflect light at wavelengths below a selected wavelength or range of wavelengths (e.g., below about 750 nm) and to transmit light at longer wavelengths.

The first dichroic mirror 19 is preferably constructed to reflect wavelengths above a selected wavelength, including the wavelength of the light in the beam 12 from the source 11, and to substantially transmit wavelengths below the selected wavelength. The specimen 22 contains a fluorophore(s) suited to absorb two (or more) photons at the wavelength of the source 11 and to fluorescently emit shorter wavelength photons. These photons are emitted in all directions from the focal point of the beam 12 within the specimen 22. About half of these photons are emitted in a direction to be captured by the objective lens 20 and are redirected on a beam path 33 to the first dichroic mirror 19. Because the wavelength of the photons in the beam 33 is below the selected cross-over wavelength of the first dichroic mirror 19, the beam 33 passes through the dichroic mirror 19 and is focussed by a lens 34 onto a photodetector 35 (e.g., a photomultiplier tube). An excitation source blocker (not shown) may also be inserted in the beam 39 to further protect the detector 35 from source wavelengths (e.g., a 1047 nm excitation source blocker, RE950SP from Chroma). The photodetector provides an electrical output signal to a controller processor 37 of the scanning microscope system 10 which stores and processes the signal from the photodetector 35 in a standard fashion for such microscopes and which can display the image picked up by the photodetector 35 on a display device 38, such as a video display terminal. The controller processor 37 also controls the scanning of the x-y scanner 13 in a conventional fashion.

To enhance the collection of the fluorescent photons from the specimen 22, it is preferred that oil immersion optics be used at the condenser 25, as illustrated in FIG. 1, to minimize condenser path losses and to maximize signal enhancement collection.

Fluorescent photons are emanated in all directions from the spot in the specimen 22 at which the incoming beam 12 is focussed. Some of these photons emitted from the specimen pass through the transparent support substrate 23 toward the condenser lens 25, and these photons are collected by the condenser lens into a beam so as to be incident upon the flat face of the dichroic mirror 30. Because the fluorescent photons are at a wavelength less than the selected cross-over wavelength of the second dichroic mirror 30 (e.g., less than about 750 nm), the emission photons are reflected by the mirror 30 (the reflected photons are illustrated by the beam labeled 39 in FIG. 1) back into the condenser lens 25, wherein they are focussed to pass through the substrate 23 and the specimen 22 and be incident upon the objective lens 20. The fluorescent light photons in the beam 39 add to the fluorescent photon flux in the beam 33, and both the beams 33 and 39 pass through the first dichroic mirror 19 and thus are incident upon the photodetector 35. The photodetector 35 provides an output signal to the controller processor 37 that is proportional to the intensity of the photon flux incident thereon, thereby substantially enhancing the sensitivity of the microscope system for a given intensity of the incident light beam 12. Because two photon (or multi-photon) excitation fluorescence imaging only requires that the fluorescent light photon flux be detected by the photodetector 35, any scattering of fluorescence light or misalignment of the light in the beams 33 and 39 does not substantially affect the quality of the signal provided by the photodetector. Thus, for example, it is not necessary that the condenser lens 25 precisely focus the fluorescent light reflected from the second dichroic mirror 30 into the same spot in the specimen 22 from which the fluorescent light emanated.

Utilization of the second dichroic mirror 30 in accordance with the present invention does not require substantial or expensive modifications of existing two-photon fluorescence microscopy systems. For example, the components of the microscope 10 shown in FIG. 1 may be entirely conventional, commercially available components and systems, with the only change being the addition of the second dichroic mirror 30, preferably mounted at the field iris 31. However, it is preferred that the various reflecting mirrors in the excitation beam path have enhanced silver coatings (available from Chroma) for enhanced infrared reflectivity and optimized emission throughput from 400 nm to 750 nm. The mirror 30 is preferably removable or mounted on a slider or holder so that it can be moved out of the way to allow bright field imaging with a (e.g., tungsten) lamp (not shown) in a conventional fashion. An exemplary source 11 is a Nd:YLF laser providing, for example, a 1 mm diameter beam which is expanded to an 8 mm beam by the eyepiece and achromat optics 17, providing 175 femtosecond (fs) pulses at a selected repetition rate, e.g., at a wavelength of 1047 nm, and at a laser power of about 800 mw with imaging powers at about 50 mw or less. Appropriate sources, e.g., lasers, with longer (or shorter) pulses or continuous beams may also be used, as desired. A scanning system may be utilized as described in the aforesaid U.S. Pat. Nos. 5,032,720 or 5,034,613, or confocal microscope type scanning systems commercially available from several manufacturers may be used, and the microscope optics, including the objective lens 20 and condenser lens 25, may be standard microscope optics (and may each constitute more than one lens element) available from several microscope manufacturers.

Figure 4:
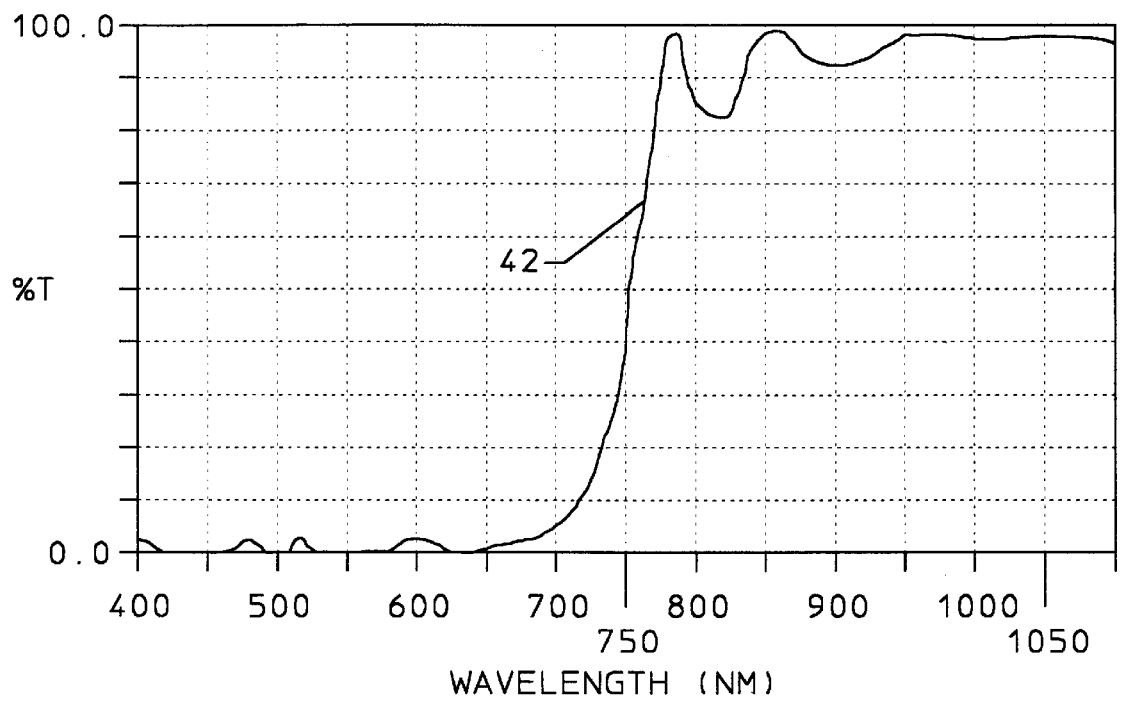
FIG. 4 is a graph showing percent of light transmission through a commercially available dichroic mirror that may be used for the second dichroic mirror of the present invention.

For an exemplary light source 11 providing an output beam at 1047 nm, a preferred second dichroic mirror 30 comprises a one piece flat mirror having a flatness on the order of one wavelength (at 633 nm), and a surface coating thereon which provides a reflectance of greater than 90 percent from 400 nm to 700 nm, and a reflectance less than 5 percent at 1047 nm at normal incidence. Suitable reflectance mirrors are available from Chroma Technology, Inc. of Brattleboro, Vt. A graph showing the percent transmission of such a preferred second dichroic mirror 30 is illustrated by the graph labeled 42 in FIG. 4. As illustrated therein, such a dichroic mirror has substantially 100 percent transmission of wavelengths over about 1,000 nm and substantially total reflectance and no transmission of wavelengths below about 700 nm. Thus, a second dichroic mirror 30 having the transmission characteristic curve illustrated in FIG. 4 would essentially pass all of the light at the source wavelength that is incident upon it, and substantially fully reflect fluorescent light in the 400 to 700 nm wavelengths.

The first dichroic mirror 19 may be a dichroic mirror design of the type used in, e.g., confocal microscopes that transmits short wavelength light and reflects longer wavelength light (e.g., 850 DCSP available from Chroma). Of course, the first dichroic mirror may alternatively reflect short wavelengths and transmit long wavelengths with a suitable rearrangement of the positions of the detector 35 and source 11. As used herein, dichroic mirror includes prisms and other optical components with dichroic reflecting surfaces as well as flat mirrors.

Figure 2:
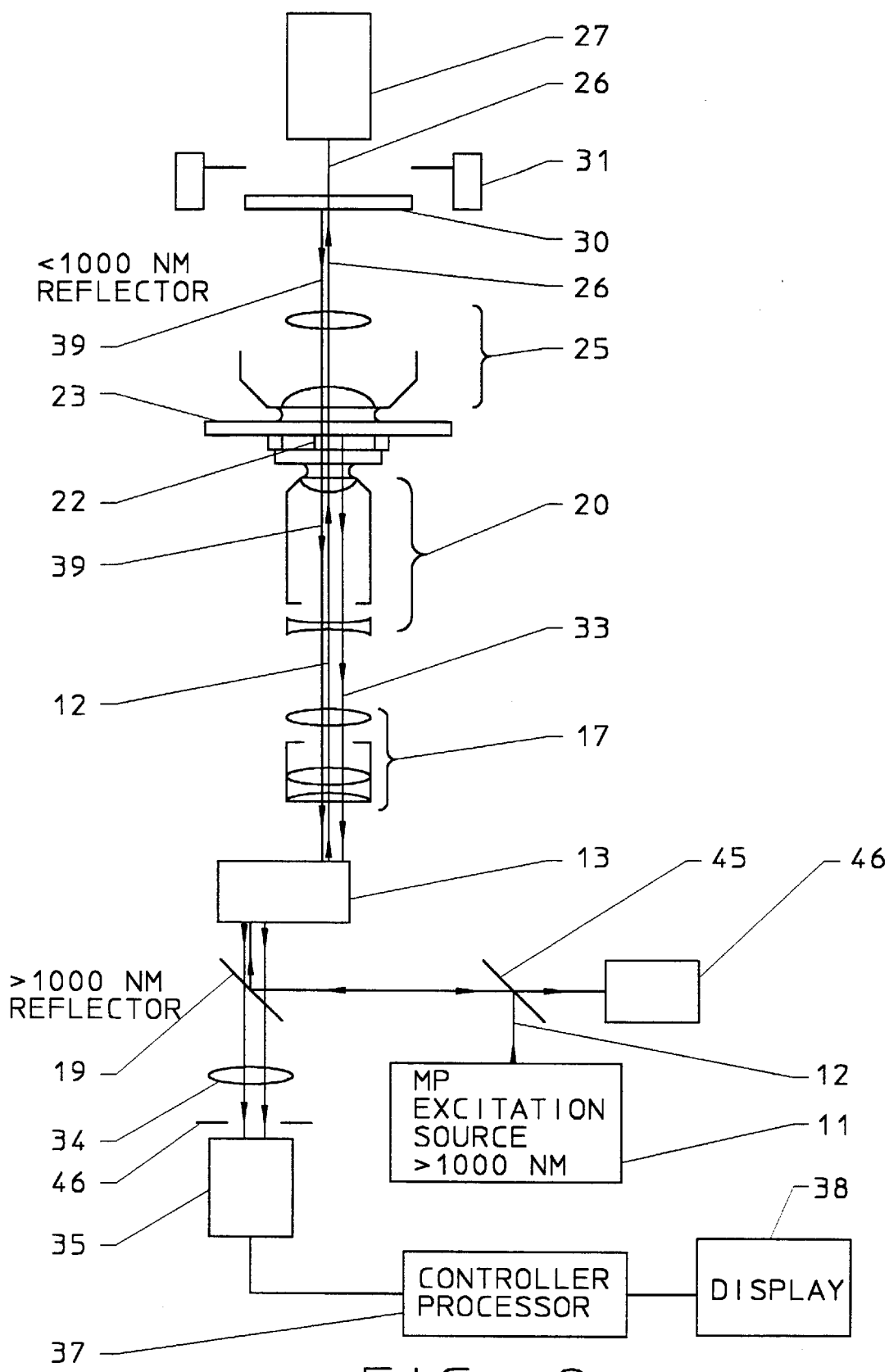
FIG. 2 is a schematic diagram of another, descanned emission, arrangement of a scanning fluorescence microscope in accordance with the invention.

The optical arrangement of FIG. 1 allows the reflected fluorescence beams 33 and 39 to pass directly through the first dichroic mirror 19 to the photodetector 35 without requiring descanning of the fluorescent light beams. Alternatively, the fluorescent light can be detected by a fluorescent light detector after the fluorescent light beams have been descanned, as illustrated in FIG. 2. In this microscope scanning system arrangement, the output beam 12 from the source 11 is directed to a first dichroic mirror 19 (either directly or after reflection from a mirror 45 as shown in FIG. 2, if desired), which performs the same function as the first dichroic mirror 19 of FIG. 1, and then is deflected by a scanning system 13 and passed through the optics 17, from which the beam passes into the objective 20 of the microscope (other conventional optical elements for reflection confocal microscope systems are not shown in FIG. 2 for simplicity of illustration). Conversely, the fluorescent light in the beams 33 and 39 that exits from the objective lens 20 that passes through the scanning system 13 is substantially "descanned" and stationary in space when incident upon the first dichroic mirror 19. Because the beams 33 and 39 are substantially stationary in space after being descanned, a confocal type pinhole aperture 46 may be utilized ahead of the photodetector 35 of FIG. 2, if desired, but generally such a confocal aperture is not preferred since it reduces the total photon flux incident upon the detector 35 and is usually not necessary because of the depth resolution that is inherently obtained in multi-photon excitation.

Figure 3:
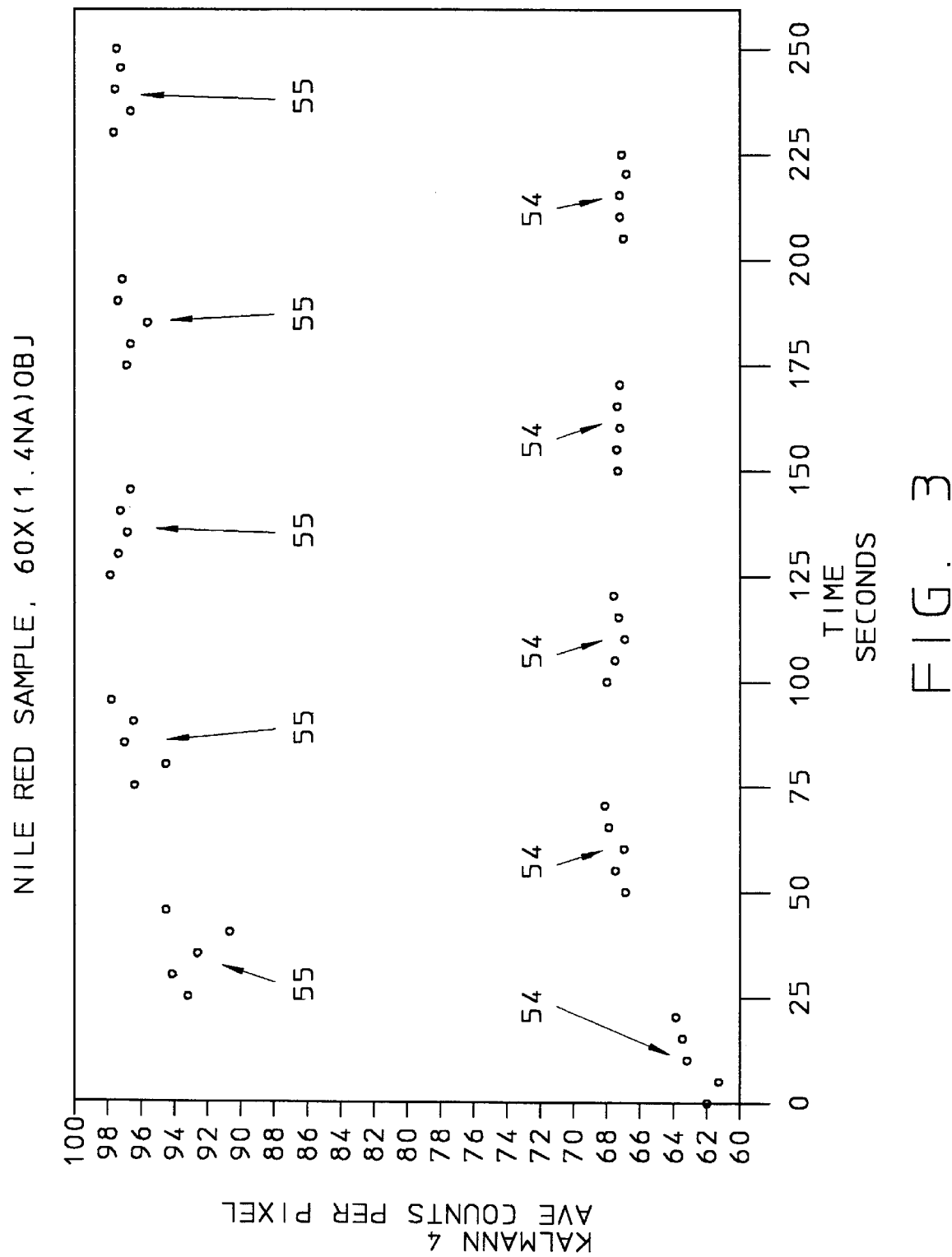
FIG. 3 are graphs showing the intensity as a function of time of the fluorescent light signal received by a photodetector from a specimen containing fluorophores in a standard two-photon scanning fluorescence microscope configuration and in the scanning fluorescence microscope configuration of the present invention as in FIG. 1.

The graph of FIG. 3 illustrates the improved fluorescence signal intensity obtained from the present invention as compared with a non-descanned or direct detection two-photon scanning fluorescence microscope as in FIG. 1. The various datapoints shown in FIG. 3 show the average photodetector pixel count for a one second scan over a specimen, with the scan repeated every five seconds five times to form a cluster of data. The fluorophore utilized in the sample was Nile Red. The fluorescence scanning system illustrated in FIG. 1 was operated in two configurations to obtain the data. In the first configuration, the second dichroic mirror 30 was removed so that the system of FIG. 1 functioned in a standard prior art configuration. For this configuration, the clusters of data indicated at 54 in FIG. 3 were obtained. In the second configuration, the second dichroic mirror 30 was in place at the field iris as shown in FIG. 1, and the clusters of datapoints labeled 55 in FIG. 3 were obtained. In both configurations, a 60× microscope objective 20 was used having a numerical aperture of 1.4. The data of FIG. 3 show approximately a 43 percent increase in the intensity of the signal at the fluorescence detector 35 with the second dichroic mirror 30 in place compared to the conventional configuration for the microscope system. It is also found that the present invention yields a significant improvement in intensity over conventional configurations at all depths of focus within a (100 $\mu$m thick) specimen as illustrated in FIG. 5.

Figure 5:
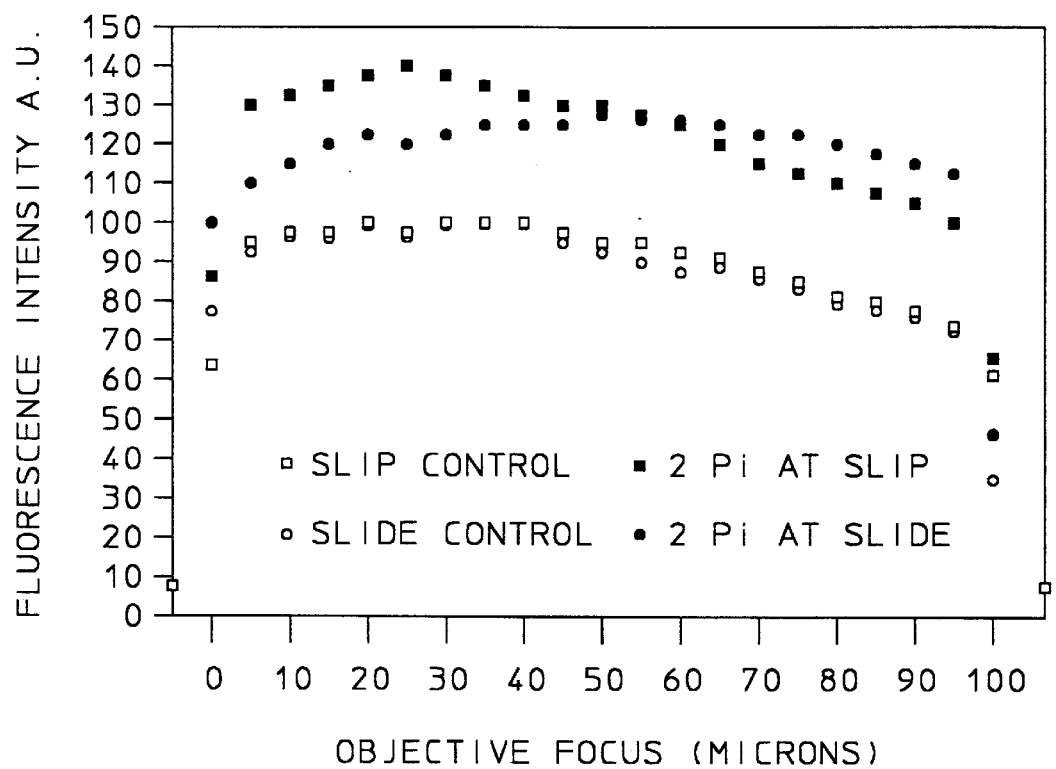
FIG. 5 are graphs illustrating the collection enhancement depth of field obtained in accordance with the invention in the configuration of FIG. 1.

The collection enhancement depth of field with condenser lens fluorescence reflection is also demonstrated in FIG. 5. The squares represent data taken with the condenser lens focused 10 $\mu$m in from the cover slip, while the circles represent data taken with the condenser lens focused 90 $\mu$m in from the cover slip (near the microscope slide). The filled symbols represent data taken with the dichroic reflector 30 installed, while the open symbols represent data (controls) taken with the dichroic reflector 30 removed. In principle, the additional condenser collection can give up to 100% signal enhancement; in practice, 50% enhancement was obtained due to losses in the condenser optics. However, the condenser focus (depth of field) is not critical to the enhancement effect. Focusing the condenser lens and the objective near the coverslip provides 40% improvement, but the enhancement is still effective when the objective lens is focused 100 $\mu$m away from the condenser lens. Interestingly, when the condenser lens is focused near the microscope slide the enhancement effectively compensates for signal falloff encountered as the objective lens focuses into the lightly scattering sample. The two control Z-series without the second dichroic mirror 30 yield very similar values and demonstrate the normal direct detection MPEM signal decay into the sample.

In general, it is preferred that the objective lenses used be designed or selected for high NA, better scattering throughput, higher transmission visible/near IR lens coatings, and flat fields while retaining as long a working distance as possible. It is also preferred to use anti-reflection coatings on the condenser lens(es).

Table 1 illustrates the signal enhancement obtained in accordance with the invention for various objective lenses as denoted in the table. In each case, a 1.4 NA oiled condenser lens 25 was used. The data illustrate the significant difference in signal level for each objective when the reflector (mirror) 30 is in and when it is out, for both FIG. 1, and FIG. 2, with and without the pinhole aperture 45 shown in FIG. 2.

TABLE 1

| MAG | OBJECTIVE LENS | NA | CONDENSER FIG. 1 | ENHANCEMENT FIG. 2 no pinhole | FIG. 2 w/pinhole |
|---|---|---|---|---|---|
| 10X | Plan Apo | 0.45 | 60% | 60% | 110% |
| 20X | Plan Fluor | 0.75 | 65% | 90% | 100% |
| 40X | Plan Fluor | 1.3 | 44% | 35% | 250% |
| 60X | Plan Apo | 1.4 | 50% | 12% | |

It is understood that the invention is not confined to the embodiments set forth herein as illustrative, but embraces all such forms thereof as come within the scope of the following claims.

What is claimed is:

1. A multi-photon fluorescence microscope comprising:
   (a) a light source providing a source beam of light that includes a chosen long wavelength;
   (b) a microscope objective lens receiving the beam from the light source, the objective lens focussing the beam to a narrow point at which a specimen may be positioned;
   (c) a fluorescent light detector;
   (d) a first dichroic mirror positioned in an optical path between the objective lens and the fluorescent light detector, the first dichroic mirror formed to receive the multi-photon absorption fluorescent light photons that are emitted from the specimen at a wavelength shorter than the chosen long wavelength of the source beam and collected by the objective lens and to direct these photons on an optical path to the detector, the detector positioned with respect to the first dichroic mirror so that the detector receives the fluorescent light emitted from the specimen and does not detect light reflected from the specimen or light in the beam from the source;
   (e) a condenser lens on the opposite side of the position of a specimen from the objective lens; and
   (f) a second dichroic mirror positioned behind the condenser lens so that fluorescent light photons entering the condenser lens from the specimen are collected by it and directed to the second dichroic mirror which is formed to reflect wavelengths shorter than a selected wavelength, with the reflected wavelengths including the fluorescent light wavelength, and to pass light at wavelengths longer than the selected wavelength, with the passed wavelengths including the wavelength of the source beam, wherein the fluorescent light photons reflected from the second dichroic mirror are collected by the condenser and are passed back through the specimen and then through the objective lens and along the optical path of the microscope to the first dichroic mirror which directs such photons to be incident on the fluorescent light detector.

2. The fluorescence microscope of claim 1 including a scanning means receiving the beam from the source for scanning the beam in a raster fashion onto the objective lens.

3. The fluorescence microscope of claim 2 wherein the first dichroic mirror is positioned to receive the rastered beam from the scanning means and to reflect the rastered beam at the wavelength of the light from the source onto the objective lens, the first dichroic mirror formed to pass wavelengths of light therethrough at selected wavelengths shorter than the wavelength of the beam from the source which include wavelengths of multi-photon absorption fluorescent light emitted from a specimen.

4. The fluorescence microscope of claim 2 wherein the first dichroic mirror is positioned to receive the beam of light from the source and reflect the beam to the scanning means and to receive multi-photon absorption fluorescent light that has passed back from the objective lens on the optical path to the scanning means, wherein the scanning means de-rasters the fluorescent light passed therethrough to the first dichroic mirror, the first dichroic mirror passing wavelengths of light shorter than the wavelength of the source beam including the wavelengths of the fluorescent light passed back through the scanning means.

5. The fluorescence microscope of claim 1 wherein the second dichroic mirror is mounted at a conjugate of the focal plane in the specimen at which light passed through the condenser lens from the specimen is focussed.

6. The fluorescence microscope of claim 1 wherein the light source is a pulsed laser providing light in the range of red to near-infrared wavelengths.

7. A multi-photon fluorescence microscope comprising:
   (a) a light source providing a source beam of light that includes a chosen long wavelength;
   (b) a microscope objective lens;
   (c) scanning means receiving the beam from the source for scanning the beam in a raster fashion onto the objective lens, the objective lens focussing the beam to a narrow point at which a specimen may be positioned;
   (d) a fluorescent light detector;
   (e) a first dichroic mirror positioned in an optical path between the objective lens and the fluorescent light detector, the first dichroic mirror formed to receive the multi-photon absorption fluorescent light photons that are emitted from the specimen at a wavelength shorter than the chosen long wavelength of the source beam and collected by the objective lens and to direct these photons on an optical path to the detector, the detector positioned with respect to the first dichroic mirror so that the detector only receives the fluorescent light emitted from the specimen and does not detect light reflected from the specimen or light in the beam from the source;
   (f) a condenser lens on the opposite side of the position of a specimen from the objective lens; and
   (g) a second dichroic mirror positioned behind the condenser lens so that fluorescent light photons entering the condenser lens from the specimen are collected by it and directed to the second dichroic mirror which is formed to reflect wavelengths shorter than a selected wavelength, with the reflected wavelengths including the fluorescent light wavelength, and to pass light at wavelengths longer than the selected wavelength, with the passed wavelengths including the wavelength of the source beam, wherein the fluorescent light photons reflected from the second dichroic mirror are collected by the condenser lens and are passed back through the specimen and then through the objective lens and along the optical path of the microscope to the first dichroic mirror which directs such photons to be incident on the fluorescent light detector.

8. The fluorescence microscope of claim 7 wherein the first dichroic mirror is positioned to receive the rastered beam from the scanning means and to reflect the rastered beam at the wavelength of the light from the source onto the objective lens, the first dichroic mirror formed to pass wavelengths of light therethrough at selected wavelengths shorter than the wavelength of the beam from the source which include wavelengths of multi-photon absorption fluorescent light emitted from a specimen.

9. The fluorescence microscope of claim 7 wherein the first dichroic mirror is positioned to receive the beam of light from the source and reflect the beam to the scanning means and to receive multi-photon absorption fluorescent light that has passed back from the objective lens on the optical path to the scanning means, wherein the scanning means de-rasters the fluorescent light passed therethrough to the first dichroic mirror, the first dichroic mirror passing wavelengths of light shorter than the wavelength of the source beam including the wavelengths of the fluorescent light passed back through the scanning means.

10. The fluorescence microscope of claim 7 wherein the second dichroic mirror is mounted at a conjugate of the focal plane in the specimen at which light passed through the condenser lens from the specimen is focussed.

11. The fluorescence microscope of claim 7 wherein the light source is a pulsed laser providing light in the range of red to near-infrared wavelengths.

12. A method of multi-photon fluorescence microscopy comprising the steps of:

(a) passing multi-photon excitation light having a chosen excitation wavelength through an objective lens of a microscope to focus the light in a specimen and excite multi-photon fluorescence emissions from a fluorophore in the specimen;

(b) collecting fluorescent light emitted directly from the specimen onto the objective lens and directing such fluorescent light to a fluorescent light detector;

(c) collecting fluorescent light emitted from the specimen by a condenser lens on the opposite side of the specimen from the objective lens, directing the fluorescent light from the condenser lens to a dichoic mirror, and reflecting the fluorescent light by the dichoic mirror back into the condenser lens and thence through the specimen and the objective lens to a fluorescent light detector while passing the excitation light through the dichoic mirror.

13. The method of claim 12 wherein the same fluorescent light detector detects the fluorescent light collected by the objective lens from the specimen and the fluorescent light reflected back through the condenser lens and the specimen to and through the objective lens.

14. The method of claim 12 wherein the multi-photon excitation light has a wavelength in the range of red to near infrared.

15. The method of claim 12 wherein the step of directing the fluorescent light from the objective lens includes passing the fluorescent light through a dichroic mirror to the detector while reflecting excitation wavelength light by the dichroic mirror.

16. The method of claim 12 wherein the step of passing excitation light through the objective lens is carried out by scanning the excitation light in a raster pattern over the objective lens to scan an area of the specimen.

17. The method of claim 16 wherein the fluorescent light directed from the objective lens to the detector is not descanned.

18. The method of claim 16 wherein the fluorescent light directed from the objective lens to the detector is descanned before being directed to the detector.

19. The method claim 16 includes the step of detecting the excitation light that has passed through the specimen and the dichoic mirror.

* * * * *